(12) United States Patent
Brady

(10) Patent No.: US 6,554,839 B2
(45) Date of Patent: Apr. 29, 2003

(54) STEPPED IOL INSERTION CARTRIDGE FOR INSERTING AN INTRAOCULAR LENS IN AN EYE

(75) Inventor: Daniel G. Brady, San Juan Capistrano, CA (US)

(73) Assignee: Advanced Medical Optics, Inc., Santa Ana, CA (US)

(*) Notice: Subject to any disclaimer, the term of this patent is extended or adjusted under 35 U.S.C. 154(b) by 0 days.

(21) Appl. No.: 09/770,868

(22) Filed: Jan. 26, 2001

(65) Prior Publication Data

US 2002/0103491 A1 Aug. 1, 2002

(51) Int. Cl.⁷ ............................................. A61F 9/007
(52) U.S. Cl. ...................................... 606/107; 623/6.11
(58) Field of Search ........................ 606/107; 623/6.11, 623/6.12

(56) References Cited

U.S. PATENT DOCUMENTS

| | | | |
|---|---|---|---|
| 5,304,182 A | * | 4/1994 | Rheinish et al. ............ 606/107 |
| 5,702,402 A | | 12/1997 | Brady |
| 5,776,138 A | * | 7/1998 | Vidal et al. .................. 606/107 |
| 5,800,442 A | | 9/1998 | Wolf et al. |
| 5,860,984 A | * | 1/1999 | Chambers et al. ........... 606/107 |
| 5,928,245 A | | 7/1999 | Wolf et al. |
| 6,010,510 A | | 1/2000 | Brown |
| 6,056,758 A | * | 5/2000 | Vidal et al. .................. 606/107 |
| 6,254,607 B1 | * | 7/2001 | Makker et al. .............. 606/107 |
| 6,267,768 B1 | * | 7/2001 | Deacon et al. ............... 606/107 |

FOREIGN PATENT DOCUMENTS

WO        00/62712        10/2000

* cited by examiner

Primary Examiner—Kevin Shaver
Assistant Examiner—Michael B. Priddy
(74) Attorney, Agent, or Firm—Stout, Uxa, Buyan & Mullins, LLP; Frank J. Uxa; Peter Jon Gluck

(57) ABSTRACT

An intraocular lens (IOL) insertion apparatus including a cartridge with an IOL-receiving chamber, a handpiece into which the cartridge is loaded, and a plunger rod that extends through a lumen in the cartridge to reliably engage the IOL therein. The chamber is stepped in one section to cause the IOL positioned therein to assume a complex curve. A lip or projection on the plunger rod is aligned with the complex curve and intersects the IOL to reliably engage the IOL across its thickness. The cartridge may be a folding type with a pair of arcuate walls and extension wings joined at a living hinge. The stepped section of the chamber may coincide with the location of the hinge.

14 Claims, 3 Drawing Sheets

STEPPED IOL INSERTION CARTRIDGE FOR INSERTING AN INTRAOCULAR LENS IN AN EYE

BACKGROUND OF THE INVENTION

The present invention relates to apparatus and methods for inserting an intraocular lens through a small incision into an eye. More particularly, the invention relates to such apparatus and methods utilizing a plunger to displace an intraocular lens through a tubular insertion apparatus, wherein the intraocular lens is reliably and safely engaged by the plunger.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic normally includes an optically clear lens. Implantation of such IOLs into the eye often involves making an incision in the eye. Making the incision as small as possible reduces trauma and speeds healing.

IOLs are known which are foldable (deformable) so that the IOL can be inserted into the eye through an incision smaller than the diameter of the lens.

Some of the most generally accepted insertion apparatus employ a hollow insertion tube having a diameter which permits the folded IOL to pass freely through the tube without permanent deformation, and without causing the surgeon to apply excessive force to overcome friction between the walls of the insertion tube and the IOL. Excessive force can result in the premature ejection of the IOL before the surgeon is ready to position it within the patient's eye. Such an apparatus can be seen in Brady, U.S. Pat. No. 5,702,402. It would be advantageous to provide IOL insertion apparatus and methods which facilitate the passage of a folded IOL through the apparatus and the insertion of the IOL in the eye in easy, effective and controlled manner while avoiding damage to the IOL and undue trauma to the patient.

In these generally accepted apparatuses, the insertion tube is held in a handpiece which is coupled to a plunger rod. The plunger rod is moved distally through the insertion tube to urge the IOL to pass through the tube and into the eye.

An intraocular lens insertion apparatus of this type is disclosed in Brown, et al., U.S. Pat. No. 6,010,510, and includes an injector plunger having a blunt, rounded tip offset from the centerline of the plunger rod. The offset tip assures that the tip is biased downward against the bottom of the cartridge bore to help ensure proper engagement of the intraocular lens therein. However, there is a possibility that the plunger tip might ride underneath or otherwise fail to engage the intraocular lens.

There is thus a need for a more effective and safe means for engaging and displacing an intraocular lens from within an insertion apparatus.

SUMMARY OF THE INVENTION

The present invention provides an improved apparatus for inserting an intraocular lens through an incision into an eye. The apparatus operates in an environment that is similar to existing systems, with a cartridge being loaded into a handpiece, and plunger rod of the handpiece extending through a lumen in the cartridge to push an intraocular lens from an injection tube of the cartridge through an incision in the eye. The apparatus of the present invention provides structure within the cartridge and on the plunger rod that ensures positive engagement between the plunger rod and the intraocular lens to more reliably advance the intraocular lens into the eye in the desired orientation.

In one embodiment of the invention, an apparatus for inserting a foldable intraocular lens through an incision into an eye includes a cartridge having a longitudinal lumen generally arranged along an axis. The cartridge has a distal injection tube terminating in a mouth opening to the lumen, and a proximal loading end having a generally cylindrical inner surface defining a load chamber sized to contain an intraocular lens and form part of the lumen. The load chamber is configured to cause the foldable intraocular lens to conform around the inner surface substantially in a first curvature to define an inner lens face and an outer lens face. The load chamber is further configured to form a section of the intraocular lens having a second curvature centered outward of the outer lens face.

The inner surface may be radially stepped to form the section of the intraocular lens having the second curvature. In one embodiment, the inner surface of the loading end is defined by opposed arcuate walls having different radii of curvature, wherein the radially stepped configuration of the inner surface is formed between adjacent axially extending ends of the arcuate walls. Desirably, the cartridge is a folding-type cartridge with the opposed arcuate walls connected at a hinge. Furthermore, the arcuate walls may be aligned at adjacent axially extending first ends and misaligned at adjacent axially extending second ends, such that the second ends define the radially stepped configuration of the inner surface.

Another aspect of the present invention is an intraocular lens insertion apparatus comprising a cartridge, a handpiece for receiving the cartridge, and a plunger rod coupled to the handpiece. The cartridge has a non-tubular load chamber for receiving an intraocular lens defined by a generally arcuate inner surface interrupted by a radial step. The plunger rod is adapted to be displaced into the load chamber adjacent the radial step. The plunger rod may include an intraocular lens engaging end having a pair of spaced lips, wherein a first lip is aligned to pass directly over the radial step and a second lip is spaced toward an axis of load chamber. Desirably, the radial step defines a shoulder projecting into the load chamber to which the intraocular lens conforms. The shoulder is stepped radially inward from an adjacent portion of the arcuate inner surface to which the intraocular lens also conforms such that the lens is caused to curve radially inward at a section between the shoulder and the adjacent portion. In this regard, the first lip is aligned to pass over both the shoulder and the adjacent portion and transversely intersect the thickness of the intraocular lens at the section that curves radially inward. Again, the cartridge of the system may be a folding-type cartridge with a pair of opposed arcuate walls and a hinge enabling relative pivoting of the walls. The arcuate walls are opened to permit placement of the intraocular lens in an unfolded state on the inner surface, and walls may then be closed to create the load chamber and fold the intraocular lens therewithin.

These and other aspects of the present invention will become apparent in the following detailed description and claims, particularly when considered in conjunction with the accompanying drawings in which like parts bear like reference numerals.

DETAILED DESCRIPTION OF THE PREFERRED EMBODIMENTS

Figure 1:
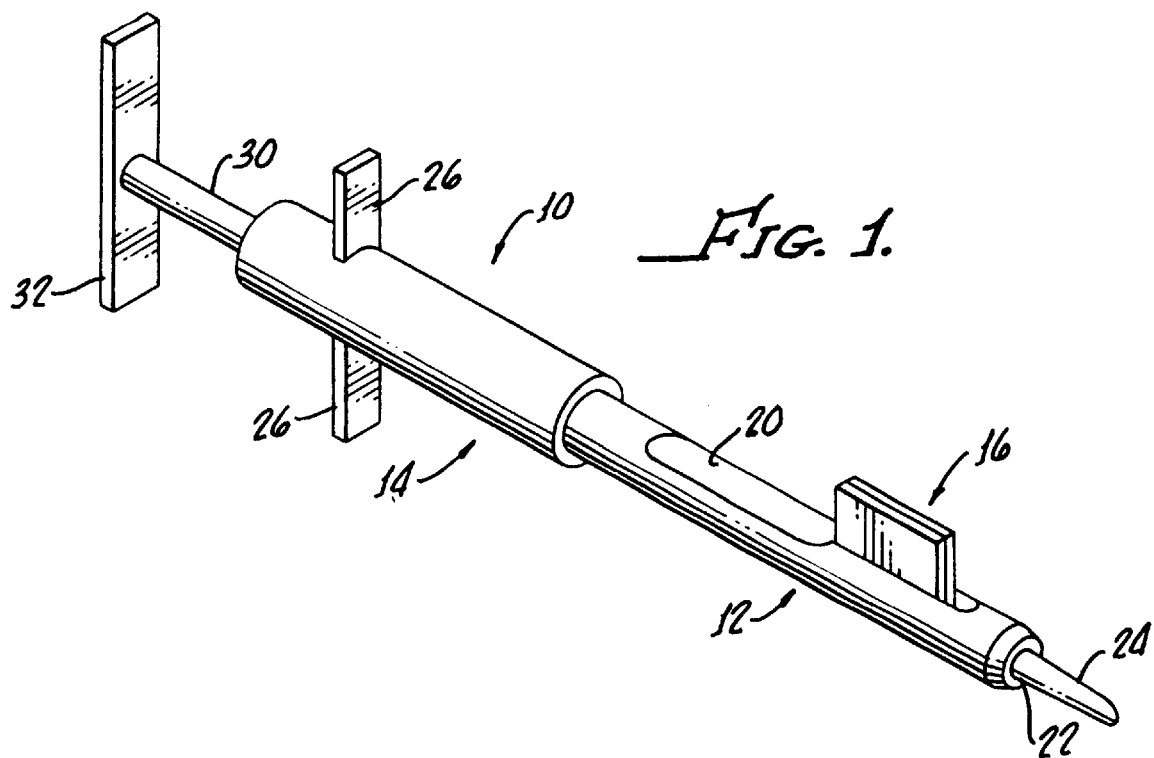
FIG. 1 is a perspective view of an intraocular lens insertion apparatus of the present invention.

FIG. 1 illustrates an IOL insertion apparatus, shown generally as 10, in accordance with the present invention. The apparatus 10 comprises a distal housing 12, a proximal housing 14 and a folding cartridge 16. Distal housing 12 is operatively coupled to proximal housing 14. Distal housing 12 includes a through opening 20 through which the folding cartridge 16 can be placed. Distal housing 12 includes a forward opening 22 through which the injection tube 24 of folding cartridge 16 extends distally. Proximal housing 14 includes two oppositely disposed finger supports 26 which extend outwardly from the outer peripheral surface 28 of the proximal housing.

Apparatus 10 also includes a plunger rod 30 which includes an enlarged proximal end 32 effective to push plunger rod 30 through proximal housing 14, as will be discussed hereinafter.

Figure 2:
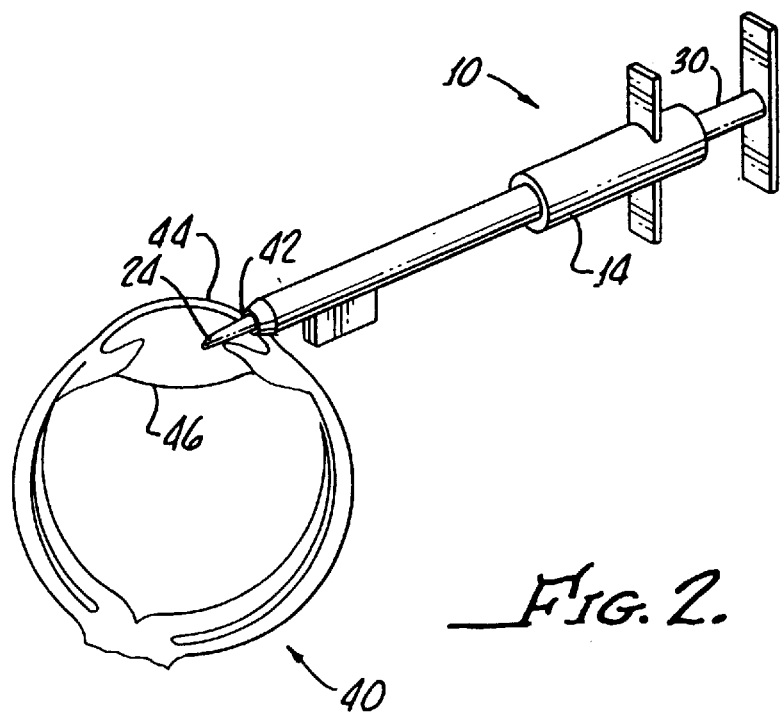
FIG. 2 is a schematic perspective drawing showing the placement of an insertion tube of the insertion apparatus of FIG. 1 in the eye.

Before proceeding to describe the operation of insertion apparatus 10, a brief description of the operation of folding cartridge 16 is provided. With reference to FIG. 2, the IOL is to be placed in the eye 40 into an area formerly occupied by the natural lens of the eye. With the IOL in its folded position within apparatus 10, as described below, injection tube 24 is ready for insertion through an incision 42 in the sclera 44 of eye 40. Capsular bag 46 protects the posterior segment of the eye 40 and as one of the eye's constituent parts which is not injured by the insertion of the IOL with the injection tube 24 inserted within the eye 40 and the distal end properly positioned, the surgeon advances plunger rod 30 by manually pushing the plunger rod 30 relative to proximal housing 14. This action moves IOL distally into injection tube 24. If needed, IOL can be repositioned in the eye by a small, bent needle or similar tool inserted into the same position.

FIG. 2 shows the sclera 44 having an incision through which the distal end portion of the injection tube 24 is passed. Alternately, the incision may be made through the cornea. Injection tube 24 preferably has a sufficiently small cross-section to pass into the eye 40 through an incision of about 3.5 mm or about 3.0 mm in the sclera 44. Once IOL is properly positioned in eye 40, and apparatus 10 is withdrawn from the eye, the incision in the sclera may be closed, for example, using conventional techniques. After use, folding cartridge 16, which is made of a polymeric material, such as polypropylene, preferably is disposed of. Remaining portions of apparatus 10, which preferably are made of metal, such as surgical grade stainless steel, may be reused after sterilization and disinfection. Any suitable material or materials of construction may be employed in the various components of the apparatus in accordance with the present invention.

Figure 3:
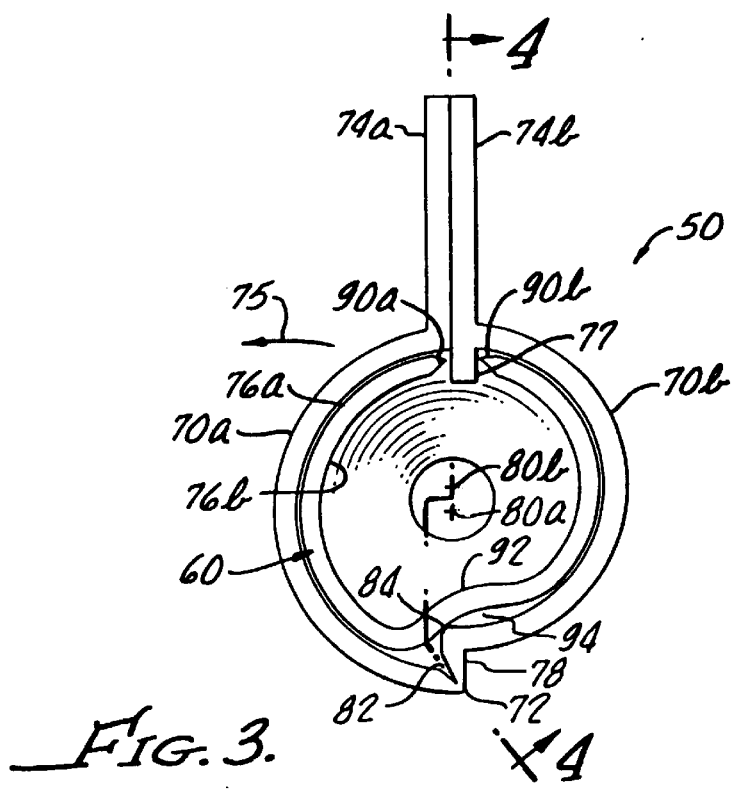
FIG. 3 is an end elevational view of a foldable cartridge of the present invention for use in an insertion system as in FIG. 1 and having an intraocular lens positioned therein.
Figure 4:
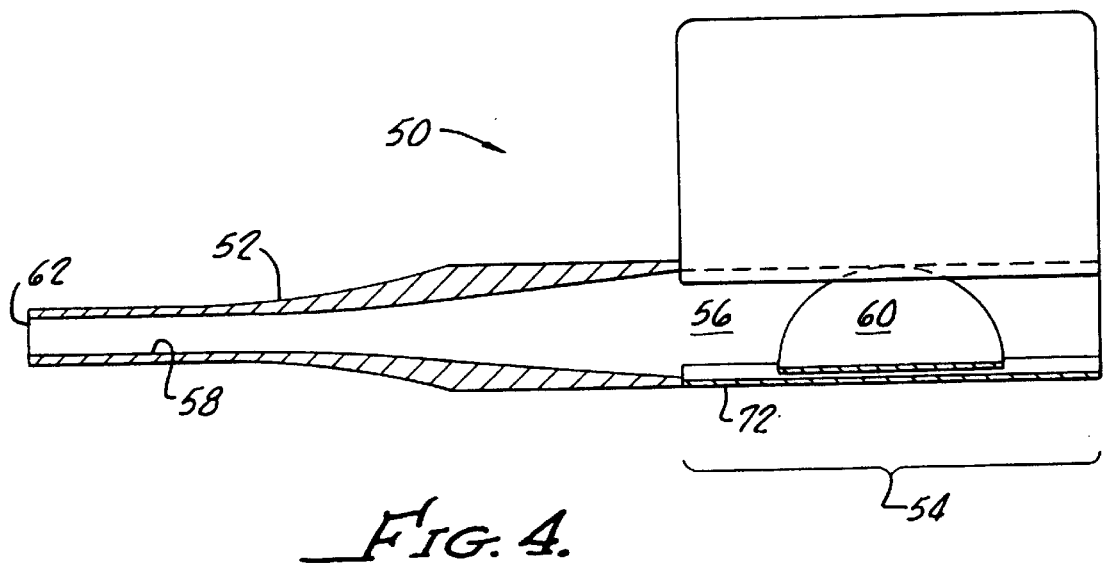
FIG. 4 is a longitudinal sectional view through the foldable cartridge taken along line 4—4 of FIG. 3.

FIGS. 3 and 4 illustrate an exemplary cartridge 50 of the present invention to be used as explained above with reference to the cartridge 16 of FIG. 1. That is, the combination of the cartridge 50 and intraocular lens (IOL) is coupled with an insertion apparatus 10 and positioned such that a distal tip of the cartridge is within the eye for delivery of the lens. It will be understood that the insertion apparatus 10 as described above is exemplary only, and the cartridge of the present invention may be utilized with other such apparatus that include a plunger rod for displacing the IOL from within the cartridge. A common problem with such devices is obtaining reliable engagement between the plunger rod and IOL, and the present invention provides an improved cartridge 50 for this purpose.

The cartridge 50 includes a distal injection tube 52, and a proximal loading end 54 defining a load chamber 56 therewithin. The injection tube 52 defines an elongate injection lumen 58 that is open to the load chamber 56 and provides a narrowing channel through which an IOL 60 passes. That is, the IOL 60 passes in the distal direction from its illustrated position within the load chamber 56 through the narrowing injection lumen 58 and out of a distal mouth 62 of the injection tube 52. As will be more fully explained below, a plunger rod extends entirely through the elongated lumen of the cartridge 50 and pushes the IOL 60 therethrough.

The cartridge 50 is desirably of the type that has relatively hinged portions for folding the IOL 60 therewithin. Specifically, the loading end 54 of the IOL 60 is defined by a pair of arcuate walls 70a, 70b pivotally connected at a living hinge 72. With reference to FIG. 3, and for orientation purposes only, the living hinge 72 is disposed axially along a lower generatrix of the loading end 54, with the arcuate walls 70a, 70b defining a stepped tubular inner surface and a generally cylindrical load chamber 56 therewithin. The upper ends of the arcuate walls 70a contact each other in a closed condition of the loading end 54, each continuing radially upward in a respective folding wing 74a, 74b. In a preferred embodiment, one of arcuate walls 70a, 70b is fixed with respect to the injection tube 52, while the other wall pivots with respect to the first wall and injection tube. In the illustrated embodiment, for example, the arcuate wall 70a shown on the left in FIG. 3 pivots about the hinge 72 away from the right-hand arcuate wall 70b in the direction of arrow 75. Although not shown, the arcuate wall 70a pivots about 180 degrees to open up the loading end 54 and permit placement of the IOL 60 therewithin. Subsequently, the arcuate wall 70a is folded in the opposite direction into the configuration shown in FIG. 3, which action also folds the IOL 60 substantially into a tube; the tube defining an inner lens face 76a and an outer lens face 76b. A rib 77 formed by a radially inward extension of one of the folding wings 74a, 74b may be provided to help retain the IOL 60 in a predetermined position during the folding operation.

The cartridge 50 of the present invention has a stepped tubular configuration as shown wherein one of the arcuate walls 70a, 70b has a larger radius of curvature than the other. In a preferred embodiment, the upper end of both of the walls 70a, 70b meet at approximately the same location, but the lower ends are misaligned. Therefore, the left side arcuate wall 70a may have a larger radius of curvature than the right side wall 70b such that the lower end of the left wall is offset below the lower end of the right wall, with a radial step 78 formed therebetween. The curvature of the left side wall 70a is centered about an axis 80a, while the right side wall 70b is centered about a different axis 80b, with both of the axes generally being positioned along a vertical midplane of the loading end 54, as oriented in FIG. 3.

The step 78 is desirably radially disposed with respect to both arcuate walls 70a, 70b, with the hinge 72 being located at a lower end thereof. In this regard, the hinge 72 is desirably created via removal of material from a step 78, and from the lower end of the left side arcuate wall 70a, to form a notch 82. In a preferred embodiment, the cartridge 50 is molded from a suitable polymer.

With respect to the contour of the load chamber 56, the step 78 creates a shoulder 84 between the inner surfaces of the arcuate walls 70a, 70b. The shoulder 84 is desirably rounded to prevent damage to the IOL 60, and projects into the load chamber 56 so as to deform the IOL into a multi-curvate (i.e., complex curve) configuration that facilitates engagement thereof by a plunger rod.

With reference still to FIG. 3, the IOL 60 includes a pair of edges 90a, 90b located at the upper end of the load chamber 56 on either side of the rib 77, and a midsection 92 located at the lower end of the load chamber. Most IOLs 60 are somewhat thicker in the midsection 92 than the edges 90a, 90b. Furthermore, the IOL 60 is flexible to enable folding, and thus conforms to the contour of the load chamber 56. Therefore, the IOL 60 closely conforms to the inner arcuate surfaces of the walls 70a, 70b, and has a first majority curvature centered within the load chamber 56. At the lower end, the shoulder 84 causes the midsection 92 of the IOL 60 to form a second curvature in the opposite direction, creating a point of inflection such that the midsection bows toward the axis of the load chamber 56. Stated another way, the second curvature at the midsection 92 is centered outward of the outer lens face 76a (FIG. 3). A separation space 94 may be created between the midsection 92 and the arcuate wall 70b because of this change in curvature and the resiliency of the material.

Importantly, the midsection 92 follows the left side arcuate wall 70a below the level of the shoulder 84 before curving upward and over the shoulder. Of course, the particular contour of the IOL 60 depends on the material, with silicone-based IOLs more closely conforming to the shape of the inner wall of the load chamber 56 than acrylic-based IOLs.

The section line 4—4 in FIG. 3 extends between the folding wings 74a, 74b and is offset in the middle of the load chamber 56 to avoid passing through the step 78 so that the elevation of the IOL 60 below the shoulder 84 is seen in cross-section in FIG. 4. Additionally, the section line 4—4 angles through the notch 82 so as to better illustrate the living hinge 72.

Figure 5:
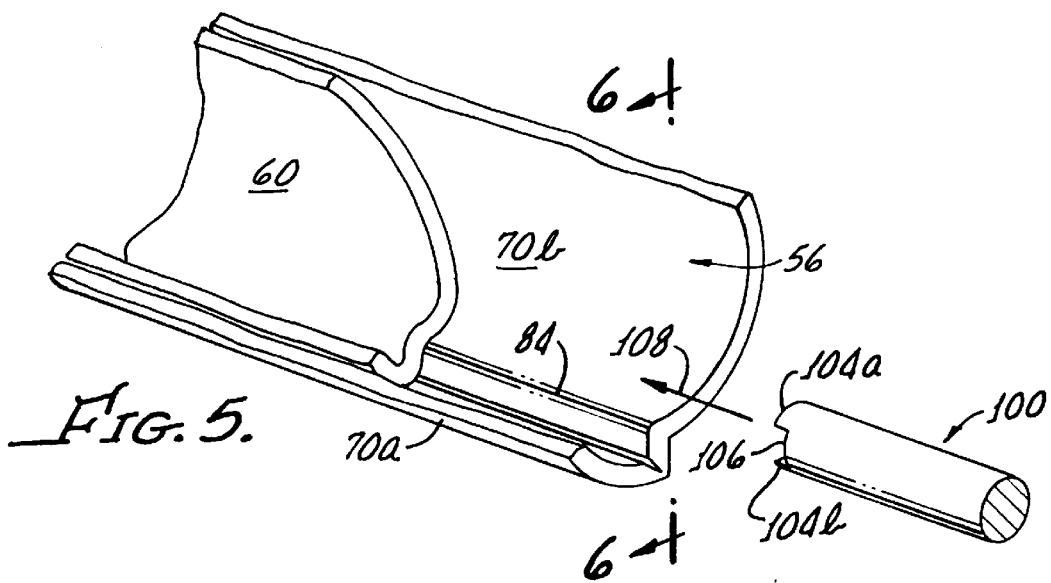
FIG. 5 is a partially cutaway perspective view of a loading chamber of the cartridge of FIG. 3 having an intraocular lens positioned therein and showing a distal tip of a plunger rod used to displace the lens through the cartridge.
Figure 6A:
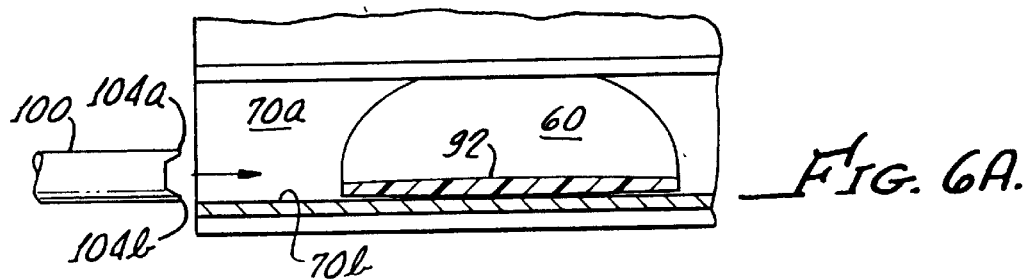
FIG. 6A is a partial sectional view taken along line 6—6 of FIG. 5 of a proximal portion of the cartridge and an intraocular lens positioned therein, prior to entry of the plunger rod into the cartridge.
Figure 6B:
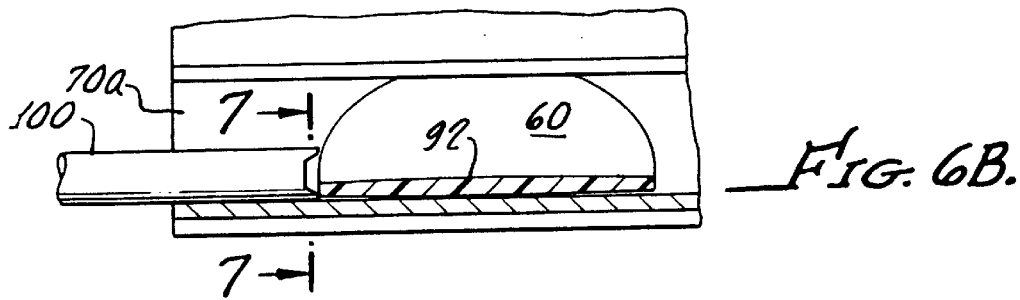
FIG. 6B is a partial sectional view as in FIG. 6A after entry of the plunger rod into the cartridge and as the rod engages the lens.
Figure 7:
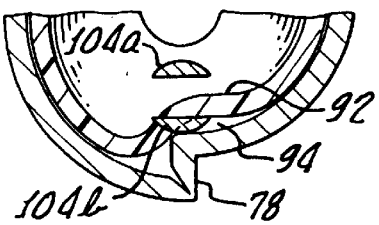
FIG. 7 is a transverse sectional view taken along line 7—7 of FIG. 6B showing the relative positions of a pair of engaging lips of the plunger rod relative to the intraocular lens at the point of engagement therebetween.

Now with reference to FIGS. 5–7, interaction of the cartridge 50 with a plunger rod 100 of an insertion apparatus (such as the apparatus 10 in FIG. 1) is shown. The plunger rod 100 may take a variety of forms, but is desirably of a type that has an IOL engaging end 102 defined by a pair of lips 104a, 104b spaced apart to define a recess 106 therebetween. Although not shown, the plunger rod 100 has a thickness and a length that permits it to extend entirely through the load chamber 56 and injection lumen 58 of the cartridge 50. In use, the plunger rod 100 engages the IOL 60 and pushes it through the cartridge 50 and from the mouth 62 into the eye of a patient.

The plunger rod 100 is rotationally oriented with respect to the cartridge 50 as shown in the figures. That is, at least until engagement with the IOL 60, lips 104a, 104b are vertically spaced apart with respect to the aforementioned orientation of the cartridge 50. FIG. 5 illustrates the direction 108 of advancement of the plunger rod 100 into the load chamber 56, which is only partially shown. Additionally, the plunger rod 100 is desirably centered with respect to the load chamber 56, and thus passes directly over the shoulder 84.

As seen in FIG. 6A, the lower lip 104b is aligned to pass closely over the arcuate wall 70b and shoulder 84. As the plunger rod 100 continues distally, as seen in FIG. 6B, the engaging head 102 eventually contacts the IOL 60 as shown. FIG. 7 illustrates the positioning of the lips 104a, 104b with respect to the midsection 92 of the IOL 60. The projection of lower lip 104b extends across the midsection 92 from the outer lens face 76a to the inner lens face 76b (see FIG. 3). Because of the curvature of the midsection 92 caused by its conformance with the shoulder 84, the lower lip 104b crosses substantially transversely to the thickness of the midsection to insure engagement therewith. In contrast, if the load chamber 56 was defined by a purely cylindrical inner surface, the lower lip 104b would be generally aligned parallel to the midsection 92, and would potentially ride over the midsection and fail to engage it. The present invention insures that the lower lip 104b extends completely across the thickness of the midsection 92 which prevents such engagement failure.

Although not shown, as the plunger rod 100 continues in the distal direction from its position shown in FIG. 6B, the IOL 60 will deform somewhat and be pushed along through the load chamber 56. Depending on the material of the IOL, the midsection 92 may eventually be captured within the recess 106 between the lips 104a, 104b. Even without such capture, the lower lip 104b is positioned so that it cannot ride over the midsection 92 by virtue of the stepped contour of the IOL 60.

While this invention has been described with respect of various specific examples and embodiments, it is to be understood that the invention is not limited thereto and that it can be variously practiced within the scope of the following claims.

What is claimed is:

1. An apparatus for inserting a foldable intraocular lens through an incision into an eye, comprising:

a cartridge having a longitudinal lumen generally arranged along an axis, the cartridge including a distal injection tube terminating in a distal mouth opening to the lumen, and a proximal loading end having a generally cylindrical inner surface defining a load chamber sized to contain an intraocular lens and form part of the lumen, the load chamber being configured to cause the foldable intraocular lens to conform around the inner surface substantially in a first curvature to define an inner lens face and an outer lens face, the load chamber being further configured to form a section of the intraocular lens wherein the outer lens face has a second curvature centered outward of the outer lens face.

2. The apparatus of claim 1, wherein the inner surface is radially stepped to form the section of the intraocular lens.

3. The apparatus of claim 2, wherein the inner surface of the loading end is defined by opposed arcuate walls having different radii of curvature, with the radially stepped configuration of the inner surface being formed between adjacent axially-extending ends of the arcuate walls.

4. The apparatus of claim 3, wherein the cartridge is a folding-type cartridge with the opposed arcuate walls being connected at a hinge.

5. The apparatus of claim 4, wherein the arcuate walls are aligned at adjacent axially-extending first ends and misaligned at adjacent axially-extending second ends that define the radially stepped configuration of the inner surface.

6. The apparatus of claim 1, wherein the cartridge is a folding-type cartridge with a pair of opposed arcuate walls and a hinge enabling relative pivoting of the arcuate walls, the arcuate walls being opened to permit placement of the intraocular lens in an unfolded state on the inner surface, and the arcuate walls being closed to create the load chamber and fold the intraocular lens therewithin.

7. The apparatus of claim 6, wherein each arcuate wall has a first end and a second end, the first ends and the second ends of the arcuate walls being juxtaposed in the closed configuration, and wherein the first ends are approximately aligned and the second ends are misaligned to form a stepped configuration of the inner surface.

8. The apparatus of claim 7, further including a radial step extending between the misaligned second ends of the arcuate walls.

9. The apparatus of claim 8, wherein the step extends generally radially with respect to a longitudinal axis of the load chamber, and the hinge is located at a radially outer end of the step.

10. The apparatus of claim 1, wherein the loading end is defined by a pair of arcuate walls hingedly connected, one of the walls having a larger radius of curvature than the other, with a first axially-extending end of each of the walls being juxtaposed with the first end of the other wall, and a second axially-extending end of each of the walls being radially offset from the second end of the other wall, a radial step being formed between the second ends and an inner shoulder thus being defined in the inner surface over which the intraocular lens conforms to form the second curvature.

11. An apparatus for inserting a foldable intraocular lens through an incision into an eye, comprising:

a cartridge having a longitudinal lumen generally arranged along an axis, the cartridge including a distal injection tube terminating in a distal mouth opening to the lumen, and a proximal loading end having a generally cylindrical inner surface defining a load chamber sized to contain an intraocular lens and form part of the lumen, the load chamber being configured to cause the foldable intraocular lens to conform around the inner surface substantially in a first curvature to define an inner lens face and an outer lens face, the inner surface being radially stepped to form a section of the intraocular lens having a second curvature centered outward of the outer lens face, the inner surface of the loading end is defined by opposed arcuate walls having different radii of curvature, with the radially stepped configuration of the inner surface being formed between adjacent axially-extending ends of the arcuate walls.

12. An apparatus for inserting a foldable intraocular lens through an incision into an eye, comprising:

a cartridge having a longitudinal lumen generally arranged along an axis, the cartridge including a distal injection tube terminating in a distal mouth opening to the lumen, and a proximal loading end having a generally cylindrical inner surface defining a load chamber sized to contain an intraocular lens and form part of the lumen, the load chamber being configured to cause the foldable intraocular lens to conform around the inner surface substantially in a first curvature to define an inner lens face and an outer lens face, the load chamber being further configured to form a section of the intraocular lens having a second curvature centered outward of the outer lens face, wherein the cartridge is a folding-type cartridge with a pair of opposed arcuate walls and a hinge enabling relative pivoting of the arcuate walls, the arcuate walls being opened to permit placement of the intraocular lens in an unfolded state on the inner surface, and the arcuate walls being closed to create the load chamber and fold the intraocular lens therewithin, each arcuate wall has a first end and a second end, the first ends and the second ends of the arcuate walls being juxtaposed in the closed configuration, and wherein the first ends are approximately aligned and the second ends are misaligned to form a stepped configuration of the inner surface, and the apparatus further includes a radial step extending between the misaligned second ends of the arcuate walls and extending generally radially with respect to a longitudinal axis of the load chamber, and the hinge is located at a radially outer end of the step.

13. An intraocular lens insertion apparatus, comprising:

a cartridge having a non-tubular load chamber for receiving an intraocular lens defined by a generally arcuate inner surface interrupted by a radial step, the cartridge is a folding-type cartridge with a pair of opposed arcuate walls and a hinge enabling relative pivoting of the arcuate walls, the arcuate walls being opened to permit placement of the intraocular lens in an unfolded state on the inner surface, and the arcuate walls being closed to create the load chamber and fold the intraocular lens therewithin, the hinge is located at a radially outer end of the step;

a handpiece for receiving the cartridge; and a plunger rod coupled to the handpiece and adapted to be displaced into the load chamber adjacent the radial step.

14. An intraocular lens insertion apparatus, comprising:

a cartridge having a non-tubular load chamber for receiving an intraocular lens defined by a generally arcuate inner surface interrupted by a radial step, the cartridge is a folding-type cartridge with a pair of opposed arcuate walls and a hinge enabling relative pivoting of the arcuate walls, the arcuate walls being opened to permit placement of the intraocular lens in an unfolded state on the inner surface, and the arcuate walls being closed to create the load chamber and fold the intraocular lens therewithin, the arcuate walls have different radii of curvature, with the radial step of the inner surface being formed between adjacent axially-extending and misaligned ends of the arcuate walls;

a handpiece for receiving the cartridge; and a plunger rod coupled to the handpiece and adapted to be displaced into the load chamber adjacent the radial step.

* * * * *